United States Patent [19]

Coker

[11] Patent Number: 4,653,486
[45] Date of Patent: Mar. 31, 1987

[54] FASTENER, PARTICULARLY SUITED FOR ORTHOPEDIC USE

[76] Inventor: Tom P. Coker, 2907 E. Joyce, Fayetteville, Ark. 72701

[21] Appl. No.: 599,679

[22] Filed: Apr. 12, 1984

[51] Int. Cl.$^4$ ............................................. A61F 5/04
[52] U.S. Cl. ............................ 128/92 YF; 128/92 YC
[58] Field of Search ............... 128/92 R, 92 B, 92 BB; 411/394, 417–421, 349, 92 YF, 92 YC

[56] References Cited

U.S. PATENT DOCUMENTS

| | | | |
|---|---|---|---|
| 71,166 | 11/1867 | Harvey | 411/394 |
| 264,479 | 9/1882 | Rogers | 411/417 |
| 395,925 | 1/1889 | Rose | 411/417 |
| 408,751 | 1/1889 | Rose | 411/394 |
| 418,844 | 1/1890 | Kay | 411/394 |
| 1,048,590 | 12/1912 | Russell | 411/417 |
| 1,274,923 | 8/1918 | Meyner | 411/394 |
| 1,933,825 | 11/1933 | Sloan | 128/84 |
| 1,951,278 | 3/1934 | Ericsson | 128/92 |
| 1,987,474 | 1/1935 | Grant | 85/47 |
| 2,121,193 | 6/1938 | Hanicke | 128/92 |
| 2,248,054 | 7/1941 | Becker | 145/52 |
| 2,267,925 | 12/1941 | Johnston | 128/92 |
| 2,293,930 | 8/1942 | Braendel | 85/47 |
| 2,329,398 | 9/1943 | Duffy | 128/92 B |
| 2,398,915 | 4/1946 | Bell | 128/92 |
| 2,490,364 | 12/1949 | Livingston | 128/92 |
| 2,537,070 | 1/1951 | Longfellow | 128/92 |
| 2,570,465 | 10/1951 | Lundholm | 128/92 |
| 2,609,604 | 9/1952 | Sprague | 32/1 |
| 2,839,815 | 6/1958 | Reeves | 27/21 |
| 2,860,675 | 11/1958 | Kauffman | 128/92 B |
| 2,937,642 | 5/1960 | Lange et al. | 128/92 |
| 2,952,254 | 9/1960 | Keating | 128/92 |
| 3,051,169 | 8/1962 | Grath | 128/92 |
| 3,083,609 | 4/1963 | Lovisek | 85/47 |
| 3,207,023 | 9/1965 | Knohl | 85/46 |
| 3,439,671 | 4/1969 | Kuntscher | 128/83 |
| 3,604,487 | 9/1971 | Gilbert | 128/92 |
| 3,719,186 | 3/1973 | Merig, Jr. | 128/305 |
| 3,748,949 | 7/1973 | Dreger | 85/41 |
| 3,862,631 | 1/1975 | Austin | 128/92 |
| 3,865,006 | 2/1975 | Massoney | 85/44 |
| 3,892,233 | 7/1975 | Vestby | 128/92 |
| 3,896,500 | 7/1975 | Rambert | 128/92 |
| 3,915,162 | 10/1975 | Miller | 128/92 |
| 3,987,499 | 10/1976 | Scharbach et al. | 31/91 |
| 4,013,071 | 3/1977 | Rosenberg | 128/92 |
| 4,175,555 | 11/1979 | Herbert | 128/92 |
| 4,261,351 | 4/1981 | Scherfel | 128/92 |
| 4,278,091 | 7/1981 | Borzone | 128/92 |

FOREIGN PATENT DOCUMENTS 854379 8/1981 U.S.S.R. ................. 128/92 YZ

Primary Examiner—C. Fred Rosenbaum
Assistant Examiner—C. W. Shedd
Attorney, Agent, or Firm—Vorys, Sater, Seymour & Pease

[57] ABSTRACT

A method and apparatus for fastening one element to another, particularly adapted for orthopedic use, wherein the fastener is structurally adapted to be driven into a member somewhat like a nail and to be secured therein by rotating the fastener through a predetermined angular displacement to secure threads on the fastener in the thus-fastened member. The fastener is thus readily removable by counter-rotating the device a like amount. In one embodiment, the fastener includes a head portion structurally adapted to receive a force axially applied to the fastener, a tip portion structurally adapted for leading the fastener into a member to be fastened, and a shank portion disposed between the head portion and the tip portion. The shank portion includes a thread-bearing zone and a thread-free zone circumferentially spaced about the shank portion which together comprise the entire circumference of the shank. The ratio of the thread-bearing zone to the thread-free zone is such that the shank portion is structurally adapted to be driven into the member to be fastened. In a preferred embodiment, the fastener includes a pair of opposed thread-bearing zones spaced intermediate a pair of opposed thread-free zones each occupying 90° of angular displacement about the shank. The angular displacement of a thread-bearing zone may lie in the range of about 120° to 240°. Such a fastener is particularly adapted for use in orthopedic procedures. Various head and shank configurations, including a thread profile particularly suited for orthopedic work, are also disclosed.

17 Claims, 23 Drawing Figures

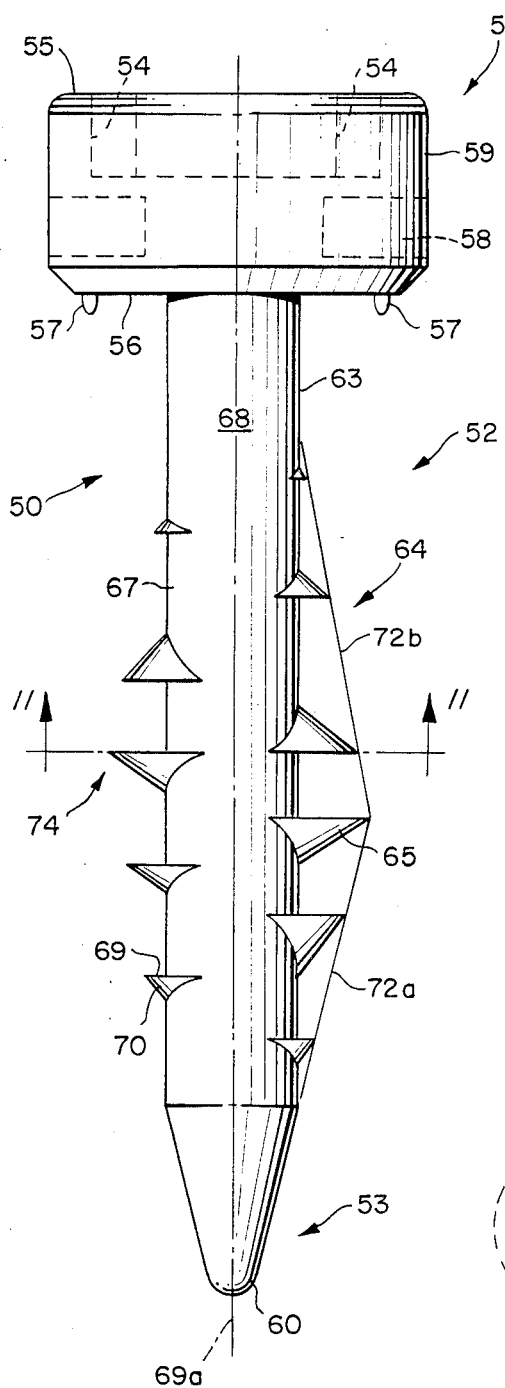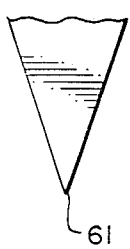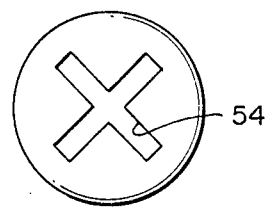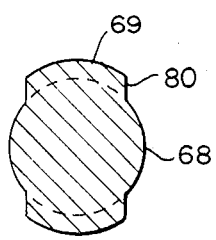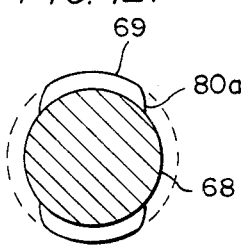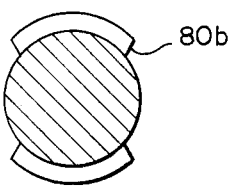

FASTENER, PARTICULARLY SUITED FOR ORTHOPEDIC USE

BACKGROUND OF THE INVENTION

This invention relates to a method and apparatus for fastening one element to another. More particularly, this invention relates to an orthopedic method and fastener for fixing tendinous ligaments to associated structures. Still more particularly, this invention relates to such a fastener suitable for use in construction, but particularly adapted for orthopedic work, which is structurally adapted to be driven into the supporting structure in a manner similar to a nail, and secured therein by rotating the device through a predetermined angle. Still more particularly, this invention relates to such a fastener having threads circumferentially located only on a limited circumferential portion of the shank of the fastener, the remaining circumferential portion being unthreaded.

In general, there are a number of applications in which a threaded fastener, such as a conventional screw, having threads substantially entirely about the circumference of the shank of the fastener, is completely satisfactory for its intended purpose. In such applications, the threaded fastener is rotated substantially continuously to advance the fastener into the support structure. For some occasions, such a technique may not be completely satisfactory. For example, in a wood construction situation having a number of screws to be fastened, it would be advantageous to be able to drive the fastener into the fastened members for purposes of quickly locking the fastener by rotation, rather than continuously rotating the screw through multiple revolutions.

In the orthopedic field of use, such a device has significant advantages. In general, in the present methods of fixing tendinous ligaments with small fragments of bone to large bones, particularly cancellous bones, screws have traditionally been the method of choice for fixation. In part, this occurs because the cortical bone is quite hard and more likely to split if the fastener is driven into it. While orthopedic staples of various types of construction have also been used, there have been advantages and disadvantages. In a typical staple construction, a groove in the top portion of the staple is used by a driver to grip the staple. Such staples are barbed to retard the staples from pulling free from the bone, but it has continued to be a problem in that frequently such staples pull free from the bone. A disadvantage in the use of the staple resides in the fact that the size of the driver is large when trying to apply a staple into a small incision such as in an interior portion of a shoulder and it can be difficult in that location to remove the staple because of the holding barbs. Thus, the more secure the barbs make the staple in the bone, the more difficult that structure makes the process for extracting the staple. Moreover, the tines can spread and bend as they are driven, sometimes causing difficulties in that the staple will penetrate a joint.

Thus, in orthopedics, an advantage of the screw is that it will not retreat and it can be easily removed by counter-rotating the screw. However, a screw is not an ideal fixation device for a tendon or ligament because the head of the screw does not tend to hold them well and it is slower to insert because of the operation time to rotate the screw to advance the fastener according to the pitch of the screw threads. Moreover, in soft tissue or with a deep incision, it is often quite difficult to locate a predrilled pilot hole for insertion of a screw.

Still another type of orthopedic fastener is a nail which can be driven quite quickly and can be barbed. However, an orthopedic nail is sometimes difficult to remove and perhaps the most difficult to drive because it is not attached to a firm, self-holding driver.

Thus, it is a general problem and a particular problem in the field of orthopedics to develop a fastener which is as quick to drive as a nail but easier to remove than a screw.

Accordingly, it is an object of this invention to provide such a fastener which features threads placed on a limited circumferential portion of the shank of the fastener so that the fastener can be driven and rotated a predetermined amount, such as a quarter of a turn, to complete the fastening process and to permit removal by counter-rotating the device a quarter of a turn.

It is an additional object of the invention to provide a method for securing two objects together by driving a fastener of the type described according to the invention into an object to be fastened through another fastening object in a manner similar to driving a nail, and securing the driven fastener by a limited rotation through a predetermined angular displacement corresponding generally to the angular distribution of a plurality of sets of threads about the circumference of the shank.

It is an additional general object of this invention to provide a fastener of the type described particularly suited for use as an orthopedic fastener.

These and other objects of the present invention will become apparent from the detailed description of the various embodiments of the invention which follow, taken in conjunction with the accompanying drawings.

SUMMARY OF THE INVENTION

Directed to achieving the above-mentioned objects and providing a fastener of the type generally described, the invention relates to a fastener suitable for use in joining a first member to a second member. The fastener is characterized by its structure which permits the fastener to be driven into such members in a manner similar to driving a nail by the application of a force axially applied to the fastener. The fastener includes a tip portion at the distal end of the fastener which is similarly structurally adapted for leading the fastener into a fastened member as the fastener is driven. A shank portion is disposed intermediate the head portion and the tip portion and includes a threaded portion which may occupy all or part of the length of the shank portion. The threaded portion of the shank includes a threaded zone and a thread-free zone circumferentially spaced about the shank. The threaded zone and the thread-free zone together comprise the entire circumference of the shank and each preferably comprises a pair of threaded sections spaced circumferentially intermediate a pair of thread-free sections. Preferably, the threaded zone occupies 180° of the circumference of the shank, while the thread-free zone also occupies 180° of the shank. However, the threaded zone may, in the aggregate, occupy as little as about 120° of the circumference of the shank and as much as 240°, as long as the fastener is otherwise able to be driven and subsequently secured by a partial rotation of the thus-driven fastener.

The ratio of the threaded zone to the thread-free zone is such that the shank portion is structurally adapted to permit the fastener to be driven into a fastened member by the application of an axial force to the fastener and to secure the members by rotating the fastener through a predetermined angular displacement to secure the threaded zone to at least one of the fastened members. The angular displacement for securing the fastener therein, after being driven, is related to the angular displacement of the threaded zones. Such a device is readily removable by counter-rotating the fastener a like distance for ready removal.

Such a fastener is particularly suited for use in orthopedics. When so used, an orthopedic fastener having the above characteristics preferably includes a head portion which is structurally adapted for a cruciate screw driver or a self-retaining screw driver and has a particular thread profile for aiding extraction. The thread profile includes threads having a radially-extending butt surface wherein the major thread diameter increases gradually between the tip portion and a predetermined intermediate portion on the shank. The diameter of the butt surface of the threads thereafter decreases between that predetermined location and the upward extent of the threads. Such a structure not only aids in the insertion of the device, but also in extracting the device from bone which has grown about the fastener during the healing process.

Various types of thread profiles, head configurations, and fractures are disclosed, along with the method of using the fastener.

BRIEF DESCRIPTION OF THE DRAWINGS

In the drawings:

FIG. 8 is a preferred embodiment of the fastener similar to FIG. 1, but particularly adapted for use in orthopedic processes;

FIG. 9 is a side view of the tip of the orthopedic fastener of FIG. 8;

FIG. 10 is a top view of the embodiment for accommodating a cruciate screw driver as a torquing element;

FIG. 11 is a cross-sectional view of the threads taken along line 11—11 of FIG. 8;

FIG. 12 is a more detailed top plan view of an alternative, preferred thread profile of one of the threads of FIG. 8 showing its cutting edge;

FIG. 12A is an alternative plan view of the thread profile similar to FIG. 11 showing an alternative, but less preferred, cutting edge;

FIGS. 13-16 show alternative head arrangements for the orthopedic fastener of FIG. 8, while

FIG. 17 shows another screw head, while FIG. 18 shows a perspective end view of a suitable mating torquing fastening element for the fastener head of FIGS. 16A and 17, while

DETAILED DESCRIPTION OF THE PREFERRED EMBODIMENTS

Figure 1:
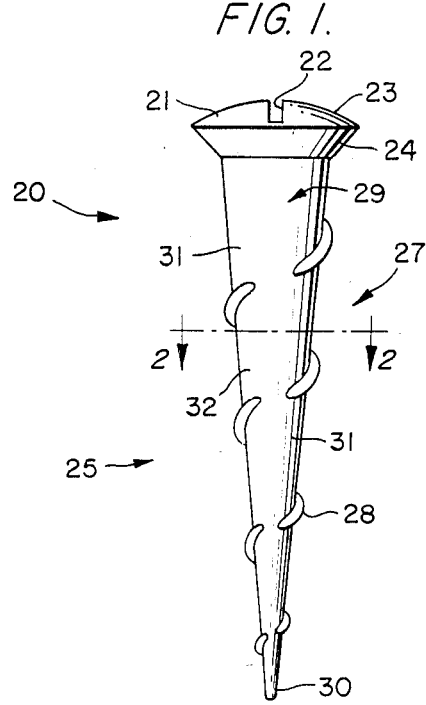
FIG. 1 is an embodiment of the fastener of the invention, similar to a conventional wood screw and suitable for fastening two members together.

In FIGS. 1-7, a preferred embodiment of the invention relating to a fastener for wood, for example, is shown in the form of a fastener designated generally by the reference numeral 20. The fastener 20 includes a head portion 21 defining an elongated kerf 22 in an upper surface 23 for receiving the tip of a screw driver (not shown) in a conventional manner, and a lower surface 24 merging into a shank portion 25 of the fastener 20. The shank 25 includes a threaded portion 27 which contains a plurality of threads 28 positioned about the shank 25, and an unthreaded portion 29 adjacent to and beneath the head portion 21. The shank 25 merges into a tip portion 30 defining an entry end of the fastener.

Together, the head portion 21, the shank 25, and the tip portion 30 resemble a conventional wood screw in physical construction. Thus, the thread pitch, length, and major and minor diameters may be varied as is well known in the art depending upon, among other factors, its intended use.

According to the invention, the threaded portion 27 of the shank portion 25 of the fastener comprises a thread-bearing zone 31 circumferentailly adjacent a thread-free zone 32 disposed about the circumference of the shank preferably for all of the length of the threaded portion 27. In this embodiment, a pair 31a, 31b of such thread-bearing zones alternate with and are spaced circumferentially intermediate a pair 32a, 32b of thread-free zones about the circumference of the threaded shank portion 27.

Preferably, each thread-bearing circumferential zone 31 extends about 90° of the circumference, so that a total of about 180° of the circumference bears threads. Conversely, each thread-free zone 32 extends circumferentially a like amount, so that the thread-bearing and thread-free zones circumferentially extend a like amount.

Figure 2:
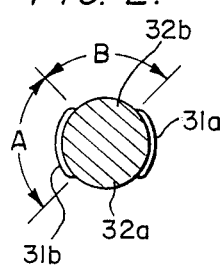
FIG. 2 is a cross section taken along line 2—2 of FIG. 1.
Figure 3:
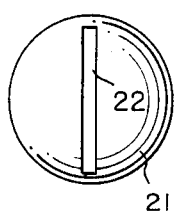
FIG. 3 is a top view of the screw of FIG. 1.
Figure 4:
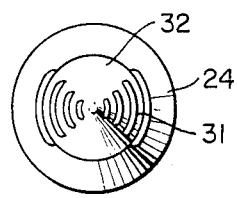
FIG. 4 is a bottom view of the screw of FIG. 1 showing a preferred disposition of adjacent threaded and thread-free sections, together defining the thread-bearing and thread-free zones.
Figure 5:
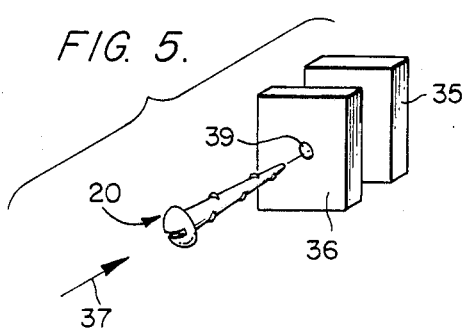
FIG. 5 is a perspective view showing the fastener of FIG. 1 posed to be axially-driven through two members.
Figure 6:
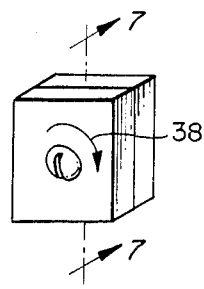
FIG. 6 is a view similar to FIG. 5 but showing the driven screw rotated through a limited angular adjacent displacement to secure the members together.

As shown in FIG. 2, the threads are disposed only about a portion of the shank of the thread-bearing zone to define opposed thread-bearing zones 31a, 31b respectively separated by opposed thread-free zones 32a, 32b in the threaded portion 27 of the shank. Preferably, the thread-bearing zones 31a, 31b, comprise about 180° of the circumference of the shank in the thread-bearing zone, while the thread-free zones 32a, 32b of the threaded portion are of like angular displacement. Thus, the fastener 20 can be axially-driven by a suitable driving device (not shown) such as a hammer, fluid-actuated gun, and the like, somewhat like a nail, axially in the direction of the arrow 37, through a member 36 into a member 35 to fasten the member 36 thereto, as shown in FIG. 5, and is rotated a quarter of a turn as shown by the arrow 38 in FIG. 6 to fix the fastener in place. After such turn, assuming a right hand thread and a clockwise turn for the embodiment shown, the thread-bearing zones 31a, 31b thus occupy and securely fix the fastener in those portions of the fastening member which were previously adjacent the thread-free zones 32a 32b, respectively.

A pilot opening 39 is shown in the member 36 of FIG. 5. However, such a pilot opening is not necessary so long as the fastener 20 is able to penetrate the member 36 completely to secure it to the member 35. The tip portion 30 is approximately pointed to guide the fastener while it is being driven into the member 36. When a pilot opening 39 is used, it should have a diameter which is less than or nearly equal to the maximum diameter of the shank at the thread-free zone so that the pilot opening is smaller than the maximum diameter of the thread-bearing zone. Thus, the threaded portion is able to penetrate the members 35 and 36 upon rotation of the fastener, as in FIG. 6, to cause the threaded portion to grip each member to retain them together.

Figure 7:
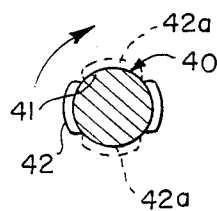
FIG. 7 is a profile of the opening in the members of FIGS. 5 and 6 defined by the driving of the fastener and relative to the disposition of the threaded zones before and after locking.
Figure 13:
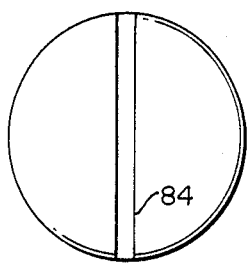
Figure 14:
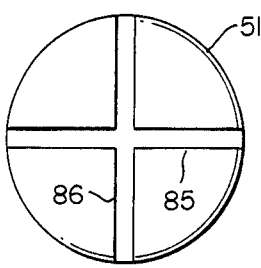

FIG. 7 shows, in the solid line 40, the contour of the opening in either of the members 36 or 35 after the fastener 20 is driven therein. A portion of the opening at the inner diameter 41 is defined by the area displaced by the thread-free zones 32a, 32b, while another portion 42 of the opening is defined by the area displaced by the thread-bearing zones 31a, 31b. The diameters 41 and 42, as shown in solid lines in FIG. 7, are together defined by the driving action of the fastener 20 into and through the member 36 and into the member 35.

The locking relationship of the threads after rotation through a quarter of a turn is shown by phantom lines 42a in FIG. 7. The profile 42a is intended to represent the positioning of the thread-bearing zones 31a, 31b after a 90° rotation into a previously unopened portion of the members 36 and 35.

The 90° rotation of the fastener is preferable for the embodiment shown having thread-bearing and thread-free zones of 180° of the threaded portion of the shank. If the proportion of threaded to unthreaded portions is greater or less than about 1:1 as shown, the rotation to lock the device will be lesser or greater in approximately the same ratio.

While the thread-bearing zones 31a, 31b have been so described, the angular displacement subtended by the thread-bearing zone may also occupy slightly more and substantially less than the 90° thus described. Thus, for example, the thread-bearing zones 31a and 31b in an alternative embodiment could each comprise an angle A (see FIG. 2) of 60° about the circumference of the shank leaving the thread-free zones 32a and 32b to comprise an angle B (FIG. 2) of 120°. It is anticipated that the use of a thread-free zone of more than 90° and up to 120° would continue to operate within the spirit of the invention, but not work as well as the preferred ranges disclosed. For example, the area of a fastened member 35 or 36 displaced by the threaded portion of the fastener 20 during driving begins to substantially exceed the portion of the member available for locking the threads after turning when the thread-bearing zone 31 is larger than an angular displacement A of 90°. On the other hand, if the thread-bearing zone exceeds an angular displacement of 90°, the area of a fastened member 35 or 36 removed when the fastener is axially-driven into the members 36 and 35 is relatively large, thus diminishing the area available for holding the thread upon rotation for locking.

For the embodiments shown, the thread profile for the threaded portion may comprise any convenient crest shape at the major diameter of the fastener, root shape at the minor diameter of the fastener, thread pitch, and contour, thus to define a convenient thread depth suitable for the intended purpose. As is well known, the thread depth is the difference between the major diameter and the minor diameter about the pitch diameter of the fastener. Moreover, the fastener may include any convenient pitch and thread angle, depending upon the type of material to which the fastener may be applied.

In FIG. 8, a preferred embodiment of the fastener incorporating the principles of this invention for use as an orthopedic fastener is shown. The orthopedic fastener 50 comprises a head portion 51, a shank portion 52, and a tip portion 53, similar to FIG. 1. The head portion 51 includes a pair of angularly spaced kerfs 54 to accommodate a cruciate screw driver in an upper surface 55 of the head portion 51 of the fastener 50. Thus, a torquing tool for rotating the fastener for locking, as described in connection with FIGS. 1–7, can be a cruciate screw driver or other suitable torquing tools as may be appropriate for turning the fastener with a head arrangement as shown in FIGS. 13–17, including the tool of FIG. 18. A lower surface 56 of the head portion 51 of the fastener 50 includes a plurality of projecting tips 57 which aid in holding ligaments, tendons, and the like in the orthopedic securing process. In addition, the head portion 51 may also include a pair of opposed inwardly projecting openings 58 in the axially-extending surface 59 for accommodating a self-retaining screw driver. Thus, the radially extending lower surface 56, the axially-extending surface 59, and the upper surface 55, together define the head portion. While the embodiment shown is described as being circular in cross section, as shown in FIG. 10, the axially-extending surface 59 may be knurled or otherwise irregular or polygonally-shaped for other types of torquing tools as may be desirable.

As shown in FIG. 8, the tip portion 53 is preferably rounded when viewed as shown by the contour 60 in FIG. 8 and relatively sharpened or pointed when viewed from the opposed side as shown by the contour 61 in FIG. 9. The purpose of the sharpened tip in the profile shown in FIG. 9 is to permit the fastener to be driven easily into the location of interest, to guide the fastener through the member to be fastened to another member, and to facilitate the driving of the fastener 50 by the application of a force axially thereto as described in connection with FIGS. 1–7.

As in the case of FIG. 1, the embodiment of FIG. 8 includes on the shank portion an unthreaded portion 63 and a threaded portion, shown generally at 64, and comprising a plurality of threads 65 having a profile which will be described in greater detail. The shank portion 52 thus comprises a thread-bearing zone 67 and a thread-free zone 68 angularly circumferentially distributed about the circumference of the shank according to the ranges described in connection with FIG. 1. In the orthopedic fastener 50, the thread profile is of greater interest in that bone continues to grow about the fastener during the healing process thus further retarding convenient withdrawal of the fastener 50 from the bone after the healing process is complete. Thus, the thread profile for the orthopedic fastener 50 is characterized over any convenient thread profile as described in connection with FIG. 1 by two particular features.

First, the thread profile of the thread 65 includes a radially-extending butt surface 69 extending approximately perpendicularly to the axis of symmetry 69a of the fastener throughout the thread-bearing zone 67. An angularly disposed thread surface 70 is inclined obliquely relative to the axis 69a to join the radially-extending butt surface 69 along a line 72 defining a variable major diameter for the threads. Thus, the major diameter of the threads along the line 72a is increasing as one traverses the fastener from the tip portion 53 toward a predetermined intermediate portion 74. Thereafter, the major diameter 72 decreases along the line 72b to the unthreaded portion 63 on the shank of the fastener.

Second, the radially-extending butt surfaces 69 in the thread sequence face the head portion 51 on the side of the shank nearest the tip portion 53 relative to the predetermined line of maximum diameter 72, whereas the radially-extending butt surfaces 69 face the tip portion along that portion of the shank intermediate the line 74 and the head portion 51. The butt surface 69 thus secures the fastener against axially fore and aft movement during the healing process, while the thread profile in the lower portion of the shank aids in the entry of the fastener 50 during the orthopedic procedure in which it is applied. Moreover the profile on the upper portion of the shank aids the extraction of the fastener during the removal process.

While the shank portion 52 of the fastener is shown as having a relatively constant diameter, the diameter of that portion may vary and slightly taper as in the case of the shank portion of FIG. 1.

FIG. 11 shows a cross section taken along line 11—11 of FIG. 8 wherein the thread-free zone 68 defines the root diameter of the fastener, the radially-outward butt surface of the thread 69 defines the major diameter (which varies as described in connection with FIG. 8), and a cutting edge of transition located therebetween, designated generally by the reference numeral 80, is shown as being defined by planes equally spaced from the axis 69 of the fastener. Thus, the cutting surface in the embodiment shown is a relatively straight line which, if extended, would act as a chord to cut the periphery of the root diameter defined by the thread-free zone 68.

Because of the need to quickly secure the fastener in bone with a convenient thread-cutting motion, it is more preferred to define a cutting surface 80a as shown in FIG. 12, which surface 80a comprises a gradual angled cutting surface defining the transition therebetween. Such an embodiment is presently greatly preferred over the disposition of the cutting edge 80b as shown in FIG. 12A, which is defined by a line radially-extending outwardly from the axis.

Figure 15:
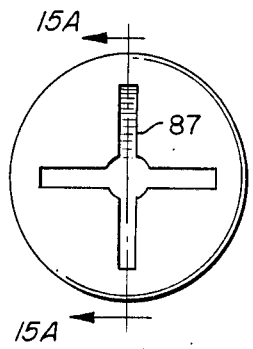
Figure 15A:
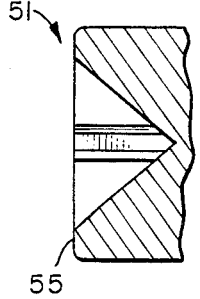
FIG. 15A is a side cross-sectional view of the head portion of FIG. 15

FIGS. 13, 14, 15, and 15A shown alternative embodiments of the head configuration of the orthopedic fastener 50. Thus, the upper surface of the head portion 51 in FIG. 13A defines a slot 84, while in FIG. 14, an alternative cruciate form is shown as defined by the perpendicularly arranged slots 85 and 86 as an alternative to the cruciate form shown in FIG. 10. In the head portion of FIG. 15, a conventional Phillips head configuration 87, as is known in the screw art, is shown and its cross section is shown in FIG. 15A.

Figure 16:
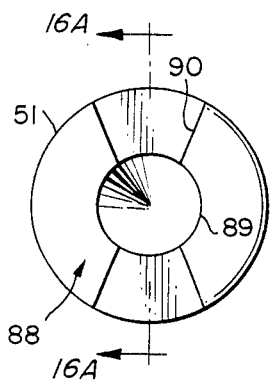

Still another alternative head form is shown in FIG. 16, wherein the upper surface 55 defines an irregularly-shaped slot 88 for receiving a like-shaped, male, mating torquing tool therein for torquing the fastener through its predetermined angular distance to secure it in the orthopedic process. Thus, the configuration 88 is defined by a conical surface 89 of revolution at about the axis 69a of the fastener 50 extending to a predetermined depth a which merges at a second depth b with the surface defined by an array of radially-extending lines 90, which extend from the radial surface 90a defined by a plane including one such line to the conical surface at the depth b. A mating torquing tool having a like configuration in a male mode can thus be applied to the surface head shown to torque the fastener 50 as previously described. An advantage of such a shape lies in the fact that the conical centrally-disposed portion of greater depth will quickly receive and seat a corresponding portion of the torquing tool while providing a bearing surface having a depth b and extending along the remaining portion of the head portion to reduce slippage and quickly rotate the fastener 50 into position to secure the thread.

Figure 16A:
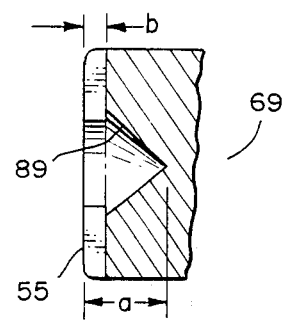
FIG. 16A is a similar side cross-sectional view of the head portion of FIG. 16.
Figure 17:
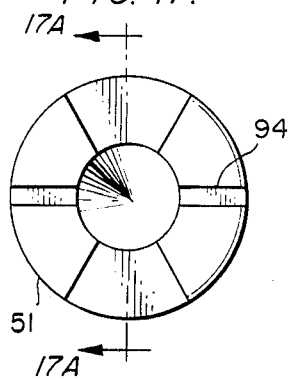
Figure 17A:
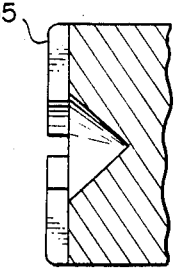
FIG. 17A is a side cross-sectional view of the embodiment of FIG. 17.

FIGS. 17 and 17A are similar to the heads shown in FIGS. 16 and 16A but with an addition of a slot 94 extending across the entire surface 55 of the head portion 51. The embodiment of FIG. 17 thus has the advantage of accommodating the male mating torquing tool applies to the embodiment of FIG. 16 or for receiving a conventional screw driver tip in the slot 92.

Figure 18A:
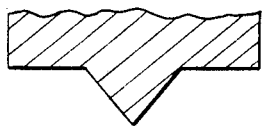
FIG. 18A is a partial cross-sectional view of the tip of the torquing element of FIG. 18.
Figure 18:
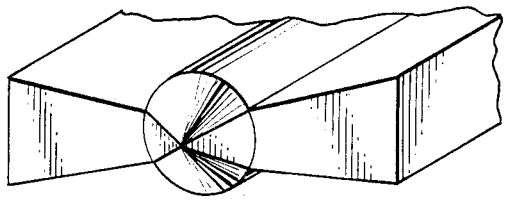

FIGS. 18 and 18A show the tip configuration for the male mating torquing tool contemplated for the embodiments of FIGS. 16 and 17, the remaining portion of the tool assuming a conventional shape for use manually, or with a pneumatic torquing machine.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. An orthopedic method for fastening a first body member such as a tendon or ligament to a second body member such as a bone by use of a fastener of the type comprising: a head portion structurally adapted for receiving a force axially applied to said fastener to drive said fastener into one of said first and second body members; a tip portion structurally adapted for leading said fastener into said one of said body members; and a shank portion comprising a threaded portion, said threaded portion comprising a thread-bearing zone and a thread-free zone circumferentially spaced about said shank portion, said thread-bearing zone and said thread-free zone together comprising the entire circumference of said shank portion, each of said zones occupying a predetermined angular displacement about said shank portion of said fastener, the ratio of said thread-bearing zone to said thread-free zone being such that said shank portion is structurally adapted to be driven into either of said first and second body members by the application of an axial force to said fastener and to secure said first body member to said second body member by rotating said fastener, after being so driven, a predetermined angular displacement to secure said thread-bearing zone in at least one of said body members, the orthopedic method being a new use for said fastener and comprising the steps of:

driving said fastener in the manner of a nail through said first body member into said second body member, and rotating said fastener in the manner of a screw while fixed in said second body member through said predetermined angular displacement to secure said fastener against withdrawal, thereby to orthopedically secure said first body member and said second body member.

2. The method as set forth in claim 1 wherein said predetermined angular displacement of said thread-bearing zone about said shank portion comprises an angle in the range of about 120° to about 240°.

3. The method as set forth in claim 2 wherein said angular displacement of said thread-bearing zone is about 180°.

4. The method as set forth in claim 3, wherein said thread-bearing zone comprises a plurality of threaded sections and said thread-free zone comprises a plurality of unthreaded sections, said threaded sections and said unthreaded sections alternating about the circumference of said shank.

5. The method as set forth in claim 1 wherein said thread-bearing zone includes threads having a profile which includes a radially-extending butt surface radially extending outwardly from said shank portion of said fastener and an outwardly flared portion, flaring outwardly along a predetermined path from said shank portion to said radially-extending portion, the intersection between said flared portion and said butt surface defining the major diameter of said threads in said threaded zone.

6. The method as set forth in claim 5, wherein said major diameter increases for a predetermined length between said tip portion and a predetermined location of maximum major diameter and gradually decreases from said predetermined location toward said head portion so that the varying major diameter thus defined aids in the extraction of said orthopedic fastener.

7. The method as set forth in claim 6, wherein the radially-extending butt surfaces of said thread profile on the lower portion of said fastener between said predetermined location and said tip are located on the side of said thread profile facing said head portion, while the butt surfaces of said thread profile between said predetermined location and said head portion are on the side of said thread profile facing said tip.

8. The method as set forth in claim 5, further including tips projecting from a surface of said head portion near said shank portion to aid in holding ligaments, tendons, and the like.

9. The method as set forth in claim 5, wherein said head portion includes means for retaining a torquing element for rotating said fastener after being driven into said body structure.

10. The method as set forth in claim 9, wherein said retaining means includes a plurality of inwardly directed openings located in an annular surface of said head portion for receiving said self-retaining screw driver.

11. The method as set forth in claim 9, wherein said head portion defines at its upper surface thereof, means for retaining said torquing element comprising one of a group consisting of a kerf, a cruciate form, and Phillips form.

12. The method as set forth in claim 9, wherein said opening is defined by an axially-located, conical inwardly-directed opening merging into a pair of opposed openings defining a bearing surface and together defining a slot in said head portion for receiving a mating torquing element.

13. The method as set forth in claim 12 further including a slot radially-extending across the top surface of said top portion and located outside of said opposed openings therein.

14. The method as set forth in claim 1, further including the step of removing said fastener by the steps counter-rotating said driven fastener through a second angular displacement equal to said angular displacement but angularly oppositely directed; and withdrawing said fastener.

15. The method as set forth in claim 1, wherein the step of rotating includes applying a torquing element having a shape mating that defined in the head portion of said fastener.

16. An orthopedic fastener for joining a first body structure member to a second body structure member, comprising:

a head portion structurally adapted for receiving a force axially applied to said orthopedic fastener to drive said fastener into one of said first and second body structure members;

a tip portion structurally adapted for leading said fastener into one of said body structure members; and a shank portion comprising a threaded portion, said threaded portion comprising a thread-bearing zone including threads having a profile which includes a radially extending butt surface, radially extending outwardly from said shank portion of said fastener, and an outwardly flared portion, flared outwardly along a predetermined path from said shank portion to said radially extending portion, the intersection between said flared portion and said butt surface defining the major diameter of said threads in said thread-bearing zone, and a thread-free zone circumferentially spaced about said shank portion, said thread-bearing zone and said thread-free zone together comprising the entire circumference of said shank portion, each of said zones occupying a predetermined angular displacement about said shank portion of said fastener, the ratio of said thread-bearing zone to said thread-free zone being such that said shank portion is structurally adapted to be driven into either of said first and said second body structure members by the application of an axial force to said fastener and to secure said first body structure member to said second body structure member by rotating said fastener, after being so driven, through a predetermined angular displacement to secure said thread-bearing zone in at least one of said body structure members, said fastener when joining said first and second body structure members passing through at least one said first and second body structure members and into the other, and wherein said major diameter increases for a predetermined length between said tip portion and a predetermined location of maximum major diameter and gradually decreases from said predetermined location toward said head portion so that the varying diameter thus defined aids in the extraction of said orthopedic fastener.

17. A fastener for use in joining a first member to a second member, comprising:

a head portion structurally adapted for receiving a force axially applied to said fastener to drive said fastener into one of said first and second members;

a tip portion structurally adapted for leading said fastener into one of said first and second members;

a shank portion comprising a threaded portion, said threaded portion comprising a thread-bearing zone including threads having a profile which includes a radially extending butt surface, radially extending outwardly from said shank portion of said fastener, and an outwardly flared portion, flared outwardly along a predetermined path from said shank portion to said radially extending butt surface, the intersection between said flared portion and said butt surface defining the major diameter of said threads in said threaded zone, and a thread-free zone circumferentially spaced about said shank portion, said thread-bearing zone and said thread-free zone together comprising the entire circumference of said shank portion, each of said zones occupying a predetermined angular displacement about said shank portion of said fastener, the ratio of said thread-bearing zone to said thread-free zone being such that said shank portion is structurally adapted to be driven into either of said first and said second members by the application of an axial force to said fastener and to secure said first member to said second member by rotating said fastener, after being so driven, through a predetermined angular displacement to secure said thread-bearing zone in at least one of said members, and wherein said major diameter increases for a predetermined length between said tip portion and a predetermined location of maximum major diameter and gradually decreases from said predetermined location toward said head portion so that the varying diameter thus defined aids in the extraction of said fastener, and wherein said radially extending butt surfaces of said thread profile on the lower portion of said fastener between said predetermined location and said tip are located on the side of said thread profile facing said head portion, while said butt surfaces of said thread profile between said predetermined location and said thread profile between said predetermined location and said head portion are on the side of said thread profile facing said tip.

* * * * *